United States Patent
Simanzhenkov et al.

(10) Patent No.: US 10,589,258 B2
(45) Date of Patent: Mar. 17, 2020

(54) CONTROLLED PRESSURE HYDROTHERMAL TREATMENT OF ODH CATALYST

(71) Applicant: NOVA Chemicals (International) S.A., Fribourg (CH)

(72) Inventors: Vasily Simanzhenkov, Calgary (CA); Xiaoliang Gao, Calgary (CA); David Jeffrey Sullivan, Calgary (CA); Hanna Drag, Calgary (CA); Marie Annette Barnes, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 71 days.

(21) Appl. No.: 15/651,366

(22) Filed: Jul. 17, 2017

(65) Prior Publication Data
US 2018/0021760 A1 Jan. 25, 2018

(30) Foreign Application Priority Data
Jul. 19, 2016 (CA) ..................................... 2936448

(51) Int. Cl.
*B01J 27/057* (2006.01)
*B01J 23/00* (2006.01)
(Continued)

(52) U.S. Cl.
CPC ......... *B01J 27/0576* (2013.01); *B01J 23/002* (2013.01); *B01J 23/28* (2013.01);
(Continued)

(58) Field of Classification Search
CPC ...... B01J 27/0576; B01J 23/002; B01J 23/28; B01J 37/0036; B01J 37/06; B01J 37/08; B01J 37/10; C07C 5/48
See application file for complete search history.

(56) References Cited

U.S. PATENT DOCUMENTS 5,021,384 A * 6/1991 Hatano .................. B01J 27/198
423/305
7,319,179 B2 1/2008 Lopez et al.
(Continued)

FOREIGN PATENT DOCUMENTS

CN 203469946 U * 3/2014 ................ B01J 3/02
DE 11 2009 000 404 T5 12/2010
(Continued)

OTHER PUBLICATIONS

Botella et al (The Preparation, Characterization, and Catalytic Behavior of MoVTeNbO Catalysts Prepared by Hydrothermal Synthesis, J Catal, (2002), 209, 445-455) (Year: 2002).*
(Continued)

*Primary Examiner* — Melvin C. Mayes
*Assistant Examiner* — Michael Forrest
(74) *Attorney, Agent, or Firm* — Julie L. Heinrich (57) ABSTRACT

The preparation of an oxidative dehydrogenation catalyst comprising Mo, V, Nb and Te using a hydrothermal step the activity and reproducibility of the catalyst is improved by conduction the hydrothermal step at higher pressures while permitting gaseous products to leave the reactor. In some instances a condenser may be upstream of the pressure relief valve.

16 Claims, 1 Drawing Sheet

(51) Int. Cl.
*B01J 23/28* (2006.01)
*B01J 37/00* (2006.01)
*B01J 37/06* (2006.01)
*B01J 37/08* (2006.01)
*B01J 37/10* (2006.01)
*C07C 5/48* (2006.01)

(52) U.S. Cl.
CPC ........... *B01J 37/0036* (2013.01); *B01J 37/06* (2013.01); *B01J 37/08* (2013.01); *B01J 37/10* (2013.01); *C07C 5/48* (2013.01); *B01J 2523/00* (2013.01); *C07C 2523/20* (2013.01); *C07C 2523/22* (2013.01); *C07C 2523/28* (2013.01); *C07C 2527/057* (2013.01); *Y02P 20/52* (2015.11)

(56) References Cited

U.S. PATENT DOCUMENTS

| | | |
|---|---|---|
| 8,105,971 B2 | 1/2012 | Gaffney et al. |
| 8,519,210 B2 | 8/2013 | Arnold et al. |
| 2008/0102025 A1* | 5/2008 | Kurth .................... B01J 3/02 423/702 |
| 2010/0255985 A1* | 10/2010 | Gaffney ................ B01J 23/002 502/312 |
| 2014/0128653 A1 | 5/2014 | Bal et al. |

FOREIGN PATENT DOCUMENTS

| | | | |
|---|---|---|---|
| DE | 10 2013 014 241 A1 | 3/2015 | |
| WO | WO-2009106474 A2 * | 9/2009 | ............ B01J 23/002 |

OTHER PUBLICATIONS

Celaya-Sanfiz et al (Preparation of Phase-Pure M1 MoVTeNb Oxide Catalysts by Hydrothermal Synthesis—Influence of Reaction Parameters on Structure and Morphology, Top Catal (2008) 50:19-32) (Year: 2008).*

Peri, J.B. and Hensley, A.L., Jr.; The Surface Structure of Silica Gel; The Journal of Physical Chemistry; vol. 72, No. 8, Aug. 1968, pp. 2926-2933.

Wen, C.Y. and Yu, Y.H.; Mechanics of Fluidization; Chemical Engineering Progress Symposium Series; No. 62, vol. 62 (1966); pp. 100-111.

* cited by examiner

CONTROLLED PRESSURE HYDROTHERMAL TREATMENT OF ODH CATALYST

The present disclosure relates to a process for the hydrothermal treatment of oxidative dehydrogenation catalysts (ODH) for lower alkanes. There are several methods to produce mixed oxide catalysts comprising Mo, V, Nb and Te suitable for use in the oxidative dehydrogenation of lower alkanes such as ethane to ethylene. One method uses a hydrothermal treatment of a slurry, suspension, gel or sol-gel of the mixed oxides. The resulting catalyst is subjected to a number of treatments including drying and calcining to produce the final catalyst. A difficulty is that the hydrothermal treatment is variable and may produce catalysts having different reactivity.

There are a number of patents which teach conducting the hydrothermal process in an autoclave. Representative of such art are the following patents.

U.S. Pat. No. 7,319,179 issued Jan. 15, 2008 to Lopez Nieto et al., assigned to Consejo Superior De Investigaciones Cientificas, Universidad Politecnica De Valencia, teaches at Col. 4 lines 1-23 that the "mixing stage may be carried out in an auotoclave. In examples 5, 7, and 11 the hydrothermal treatment is carried out in an autoclave. The patent teaches the autoclave is kept at 175° C. static for a specified period of time. This teaches away from the subject matter in the present disclosure.

U.S. Pat. No. 8,105,971 issued Jan. 31, 2012 to Gaffney assigned to Lummus Technology Inc. teaches at Col. 6 lines 6 and 7 that the admixing step may be carried out in an autoclave. No conditions are specified for the autoclave. The catalyst in the patent contains Sb and Ni which are absent from embodiments of the catalysts in the present disclosure. There are no examples of conducting the hydrothermal treatment in an autoclave.

U.S. Pat. No. 8,519,210 issued Aug. 27, 2013 to Arnould et al., assigned to Lummus Technology Inc. contains the same teaching at Col. 6 lines 25 and 26. There are no examples of the hydrothermal treatment being carried out in an autoclave.

U.S. Patent Application Publication No. 2014/0128653 in the name of Bal et al., assigned to the Council of Scientific & Industrial Research, New Delhi teaches autoclaving the titanium support for an Mo catalyst for the oxidative dehydrogenation of ethane. This teaches away from the subject matter in the present disclosure.

Published German patent application DE102013014241 teaches a MoVNbTe ODH catalyst which is prepared using a conventional hydrothermal treatment and subsequently treated with low pressure steam. This teaches away from the subject matter in the present disclosure.

Published German Patent application DE112009000404 (WO2009/106474) teaches a process for treating a calcined an ODH catalyst prepared using a hydrothermal treatment. The catalyst is treated at a pressure of at least 10 MPa and a temperature of at least 400° C. in the presence of a fluid phase is at least one compound having a molecular weight of less than 150 and at least two different elements selected from the group consisting of C, S, O and H. Preferably the fluid is selected from the group consisting of $CO_2$, $H_2O$ and $SO_2$. This teaches away from the subject matter in the present disclosure.

Interestingly paragraph 8 of DE112009000404 discloses the problem of reproducability of the catalyst in production of small scale laboratory procedures.

The present disclosure seeks to provide a process for the production of ODH catalsyts using a hydrothermal treatment in which the activity of the catalyst is good and the consistency of the catalys is improved.

Disclosed here in are processes for the synthesis of a catalyst for the oxidative dehydrogenation of paraffins via the hydrothermal treatment comprising:

i) preparing an aqueous slurry (gel, sol-gel, dispersion, or suspension) comprising Mo, V, Nb and Te salts in a molar ratio of metal elements 1:0.3 to 3; 0.05 to 0.25; and 0.08 to 0.2 at a temperature from 25° C. to 80° C. (or for example, 45° C. to 80° C.).

ii) heating slurry in a reaction vessel to a temperature from 80° to 220° C. (or for example, from 165° C. to 185° C.) at a pressure equal or above the saturated water vapor pressure at the corresponding reaction temperature, for a period of time not less than 1 hour, or for example, less than 72 hours (or for example, from 6 to 24 hours) with agitation and simultaneous removal of gaseous byproduct species produced during the reaction.

iii) letting the reactor cool and depressurizing the reactor and recovering the solid product.

In a further embodiment, the temperature of the reactor is from 150° C.-185° C.

In a further embodiment, the pressure in the reactor is from 10 psi to 190 psi (960 kPa to 1300 kPa).

In a further embodiment, optionally, there is a condenser upstream of the pressure control device.

In a further embodiment, the condenser is operated at a temperature above 0° C. and below reaction temperature.

In a further embodiment, the gaseous product species are vented from the reactor.

In a further embodiment, the gaseous species are removed from the reactor using one or more methods selected from gas absorption, gas adsorption, membrane separation, and chemicals transformation.

In a further embodiment, the time of hydrothermal treatment is from 1 to 72 hours.

In a further embodiment, the reactor is metal.

In a further embodiment, the reactor can be lined or contain glass fibers, beads, or other nucleating agents.

In a further embodiment, the lining comprises one or more of ceramic based material, a different metal, fluorocarbon polymers and combinations thereof.

In a further embodiment, the aqueous slurry comprises a molar ratio Mo, V, Nb and Te salts 1:0.5 to 1.0:0.08 to 0.20:0.10 to 0.20.

In a further embodiment, the resulting precatalyst is separated from the aqueous phase and washed with distilled water or an aqueous oxalic acid solution and drying the precatalyst (for example in an oven for not less than 6 hours at a temperature from 70° C. to 120° C.).

In a further embodiment, optionally, the dried precatalyst is ground, to a size of, for example, less than 125 μm.

In a further embodiment, the dried precatalyst is calcined in an inert atmosphere at a temperature from 200° C. to 650° C. for a time from 1 to 20 hours.

In a further embodiment, the calcined product comprises the following molar ratios: Mo 1:V 0.32-0.49:Te 0.10-0.17:Nb 0.14-0.17 as determine by PIXE.

In a further embodiment, there is provided an oxidative dehydrogenation catalyst having the empirical formula as measured by PIXE (Particle Induced X-Ray Emission analysis):

$$Mo_{1.0}V_{0.32-0.49}Te_{0.10-0.17}Nb_{0.14-0.17}O_d$$

where d is a number to satisfy the valence of the oxide

In a further embodiment, the molar ratio of Mo:V in the calcined catalyst is from 1:0.32 to 1:0.42 as measured by PIXE.

In a further embodiment the molar ratio of Mo:Te in the calcined catalyst is from 1:0.11 to 1:0.14 as measured by PIXE.

In a further embodiment, there is provided a method for the oxidative dehydrogenation of a mixed feed comprising ethane and oxygen in a volume ratio from 70:30 to 95:5 and optionally one or more $C_{3-6}$ alkanes or alkenes and oxygenated species including CO and $CO_2$ at a temperature less than 400° C., a gas hourly space velocity of not less than 100 $hr^{-1}$, and a pressure from 0.8 to 7 atmospheres comprising passing said mixture over the above catalyst.

In a further embodiment, the ODH process has a selectivity to ethylene of not less than 90%.

In a further embodiment, the gas hourly space velocity of the ODH process is not less than 500 $hr^{-1}$ or for example, not less than 1500 $hr^{-1}$ in some embodiments 3000 $hr^{-1}$.

In a further embodiment, the temperature of the ODH process is less than 385° C., or for example, less than 375° C.

In a further embodiment, the catalyst in the ODH process forms a fixed bed.

NUMBERS RANGES

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

In the specification, the phrase "the temperature at which there is 25% conversion of ethane to ethylene" is determined by plotting a graph of conversion to ethylene against temperature typically with data points below and above 25% conversion or the data is fit to an equation and the temperature at which there is a 25% conversion of ethane to ethylene is determined. In some instances in the examples, the data had to be extrapolated to determine the temperature at which 25% conversion occurred.

In the specification, the phrase "selectivity at 25% conversion" is determined by plotting the selectivity as function of temperature or fit to an equation. Then having calculated the temperature at which 25% conversion occurs one can determine either from the graph or from the equation the selectivity at that temperature.

Some embodiments of calcined catalysts prepared in accordance with the present disclosure have the formula: $Mo_{1.0}V_{0.32-0.49}Te_{0.10-0.17}Nb_{0.14-0.17}O_d$ as determined by PIXE where d is a number to satisfy the valence of the oxide. In some embodiments, the molar ratio of Mo:V in the calcined catalyst is from 1:0.32 to 1:0.42, in other embodiments the molar ratio of Mo:V in the calcined catalyst is from 1:0.36 to 1:0.40, in some embodiments from 1:0.38 to 1:0.40. In other embodiments the molar ratio of Mo:Te in the calcined catalyst is greater than 1:0.11 and less than 1:0.16, in further embodiments the molar ratio of Mo:Te in the calcined catalyst is from 1:0.11 to 1:0.14.

In some further embodiments, the catalyst may comprise a 5th component such as Sb, W, or Ni in very small amounts, for example from 0.001 to 0.001 moles.

The starting composition to be treated in accordance with the present disclosure may be prepared by a number of processes.

In one embodiment, precursor is prepared by mixing solutions or slurries (suspensions) of oxides or salts of the metallic components.

In some embodiments the precursor may be prepared by a process comprising the following steps:

i) forming an aqueous solution of ammonium heptamolybdate (tetrahydrate) and telluric acid at a temperature from 30° C. to 85° C., in some embodiments from 45° C. to 80° C. and adjusting the pH of the solution to 6.5 to 8.5, or for example, from 7 to 8, or for example, from 7.3 to 7.7 and for example with a nitrogen-containing base to form soluble salts of the metals;

ii) preparing a aqueous solution of vanadyl sulphate at a temperature from room temperature to 80° C. (or for example, 45° C. to 70° C., or for example, 55° C. to 65° C.);

iii) mixing the solutions from steps i) and ii) together;

iv) slowly (dropwise) adding a solution of niobium monoxide oxalate ($NbO(C_2O_4H)_3$) to the solution of step iii) to form a slurry (sometimes also referred to as a gel or sol-gel or a dispersion or suspension).

The slurry comprises Mo, V, Nb and Te salts in a molar ratio of metal elements Mo 1.0:V 0.3 to 3; Nb 0.05 to 0.25; and Te 0.08 to 0.20. In some embodiments the aqueous slurry has a molar ratio Mo, V, Nb and Te salts 1:0.5 to 1.0:0.08 to 0.20:0.10 to 0.20 in further embodiments the molar ratio of Mo, V, Nb and Te salts in the slurry may be 1:0.52 to 0.80:0.12 to 0.18:0.13 to 0.19.

The slurry is heated in a reaction vessel at a temperature from 80° C. to 220° C., in some instances from 150° C. to 185° C., or for example, from 165° C. to 185° C., at a pressure equal to or above the saturated water vapor pressure at the corresponding reaction temperature for a period of time not less than 1 hour, with agitation and simultaneous removal of gaseous byproduct species produced during the reaction In some embodiments, the pressure in the reactor may be above 10 psi (690 kPa) or for example, from about 140 psi to about 190 psi (965 kPa to 1300 kPa), or for example, from 140 psi to 160 psi (965 kPa to 1100 kPa. The reaction temperature may be from 150° C.-185° C. The reaction time should be greater than 1 hour, or for example, from 6 to 72 hours, or for example, from 6 to 48 hours. The pressure is maintained in the reactor by an adjustable pressure relief valve attached to the reactor vent.

In some embodiments, there may be a condenser upstream from the adjustable pressure relief valve. In some embodiments the condenser is operated at a temperature above 0° C. and below reaction temperature. At these temperatures the condenser will not condense gaseous reaction by products such as CO, $CO_2$ $SO_2$, $SO_3$ and $NH_3$. The release of these gaseous by products promotes the formation of the more active catalyst, with significantly shorter hydrothermal reaction treatments, than possible using the previously reported art of hydrothermal reaction treatment using a sealed reactor vessel. The condenser, if present, may be air or water cooled.

In some embodiments, the gaseous by products are vented from the reactor. In some cases the gaseous species are removed from the reactor using one or more methods selected from gas absorption, gas adsorption, membrane separation, and chemicals transformation. Example gas adsorbents include carbon black and zeolites.

In some embodiments, the reactor is metal, for example steel, or for example, stainless steel. The interior of the reactor may be lined with a ceramic, glass, a different metal, a polymer such as fluorocarbon polymers (e.g. TEFLON or FEP) or combinations thereof. The reactor may contain glass fibers, beads, or other nucleating agents. The nucleating agents may be irregular (such as flakes, granules, globules, filaments etc.) or regular (such as spheres, elliptical, rods (stirring bars), rectangular prisms (both right and non-right), pentagonal prisms, pyramids, etc.). The reactor may also be seeded with an ODH catalyst having a 25% conversion to ethylene at 420° C. or less, in some instances less than 400° C., in some embodiments less than 390° C. in some embodiments less than 380° C. and a selectivity to ethylene of not less than 90%, or for example, greater than 97%, or for example, greater than 98%. The seed catalyst loadings may range from 1 to 15 wt. % of the surface of the reactor (e.g., steel, TEFLON or FEP). If both inert seed particles and catalyst are used to seed the reactor the seed catalyst loadings relative to the particulates may range from 1 to 15 wt. % of the particulates.

After the reaction is completed, the reactor is cooled and vented to release the pressure in the reactor. The resulting precatalyst is separated from the aqueous phase, for example by filtration or evaporation, and washed with distilled water or a (dilute) aqueous oxalic acid solution and dried in an oven for not less than 6 hours at a temperature from 70° C. to 120° C. The precatalyst may be dried in an atmosphere of one or more inert gases or the atmosphere may contain oxygen (e.g., air). In some instances optionally, the dried precatalyst may be ground using mechanical means (e.g., a ball or roller mill) or the dried precatalyst could be subject to cryogenic grinding. The dried and ground precatalyst may in some instances be subject to sieving through a small particle size sieve to obtain a fraction having a particle size less than 250 microns, or for example, less than 125 microns.

In some instances, the precatalyst may be is treated with the equivalent of from 0.3-2.8, in some embodiments from 0.3-2.5 mL of a 30 wt. % solution of aqueous $H_2O_2$ per gram of precursor. The treatment should be in a slurry (e.g. the precursor is at least partially suspended) to provide an even distribution of $H_2O_2$ and to control the temperature rise.

The resulting dried and optionally ground and sized precatalyst is then calcined. The catalyst precursor may be calcined in an inert atmosphere at a temperature from 200° C. to 600° C. for a time from 1 to 20 hours. The purge gases used for calcining are inert gases, including one or more of nitrogen, helium, argon, $CO_2$ (for example, high purity >90%), said gases or mixture containing less than 1 vol.-% hydrogen or air, at 200 to 600° C., or for example, at 300 to 500° C. The calcining step may take from 1 to 20 hours, in some instances from 5 to 15 hours in other instances from about 8 to 12 hours, or for example about 10 hours. The resulting mixed oxide catalyst is a friable solid typically insoluble in water. In some embodiments the calcined product has a bulk density from 1.20 to 1.53 g/cc. This bulk density is based on how much 1.5 mL of pressed and crushed catalyst weighs.

The calcined catalyst product is a dry friable product typically insoluble in water. If required, the catalyst may be subject to a sizing step, such as grinding, to produce a desired particle size. Depending on how the catalyst is to be used the particle size may be different. For example, for spray drying with a support, the particle size may range from about 5 to 75 μm, in some cases from 10 to 60 μm. For use in a bed in unsupported form the particles may have a size from about 0.1 to 0.5 mm in some instances from 0.2 to 0.4 mm.

In some embodiments, the feed to the oxidative dehydrogenation reactor includes oxygen in an amount below the upper explosive/flammability limit. For example for ethane oxidative dehydrogenation, the oxygen may be present in an amount of not less than about 16 mole % or for example, about 18 mole %, or for example from about 22 to 27 mole %, or for example 23 to 26 mole %. In some embodiments, it is desirable not to have too great an excess of oxygen as this may reduce selectivity arising from combustion of feed, final products, or both. Additionally, too high an excess of oxygen in the feed stream may require additional separation steps at the downstream end of the reaction.

To maintain a viable fluidized or moving bed, the mass gas flow rate through the bed must be above the minimum flow required for fluidization, for example from about 1.5 to about 10 times $U_{mf}$ or for example, from about 2 to about 6 times $U_{mf}$. $U_{mf}$ is used in the accepted form as the abbreviation for the minimum mass gas flow required to achieve fluidization, C. Y. Wen and Y. H. Yu, "Mechanics of Fluidization", Chemical Engineering Progress Symposium Series, Vol. 62, pp. 100-111 (1966). In some embodiments, the superficial gas velocity ranges from 0.3 to 5 m/s.

The reactor may also be a fixed bed reactor.

The oxidative dehydrogenation (ODH) process comprises passing a mixed feed of ethane and oxygen at a temperature less than 420° C. in some instances less than 410° C., in some instances less than 400° C., in some instances less than 390° C., in some instances less than 380° C., in some instances as low as 375° C., at a gas hourly space velocity of not less than 100 $hr^{-1}$, for example, not less than 500 $hr^{-1}$, for example, not less than 1500 $hr^{-1}$ for example, at least 3000 $hr^{-1}$ through one or more fixed beds at a pressure from 0.8 to 1.2 atmospheres. In some embodiments the oxidative dehydrogenation reactor operates at temperatures below 400° C. for example, from 375° C. to 400° C.

The outlet pressure from the ODH reactor may be from 105 kPa (15 psi) to 172.3 kPa (25 psi) and the inlet pressure is higher by the pressure drop across the bed which depends on a number of factors including reactor configuration, particle size in the bed and the space velocity. In some embodiments, the pressure drop may be below 689 kPa (100 psi) or for example, less than 206.7 kPa (30 psi).

The residence time of one or more alkanes, for example, $C_{2-4}$ alkanes, in the oxidative dehydrogenation reactor is from 0.002 to 20 seconds.

The Support/Binder

If required, there are several ways the oxidative dehydrogenation catalyst may be supported or bound.

Example components for forming ceramic supports and for binders include oxides of titanium, zirconium, aluminum, magnesium, silicon, phosphates, boron phosphate, zirconium phosphate and mixtures thereof, for both fluidized and fixed bed reactors. In some embodiments, the fluidized bed catalyst is spray dried with the binder, which in some embodiments forms spherical particles ranging in size (effective diameter) from 40-100 μm. However, one needs to be careful to insure that the particles are sufficiently robust to minimize the attrition in the fluidized bed.

The support for the catalyst for the fixed bed may further be a ceramic precursor formed from oxides, dioxides, nitrides, carbides selected from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, yttrium oxide, aluminum silicate, silicon nitride, silicon carbide and mixtures thereof.

In one embodiment, the support for the fixed bed may have a low surface area less than 20 $m^2/g$, alternatively, less than 15 $m^2/g$, in some instances, less than 3.0 $m^2/g$ for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 $m^2/g$.

The low surface area support could be of any conventional shape such as spheres, rings, saddles, etc.

It is important that the support be dried prior to use (i.e. before adding catalyst). In some embodiments, the support may be heated at a temperature of at least 200° C. for up to 24 hours, for example at a temperature from 500° C. to 800° C. for about 2 to 20 hours, or for example, 4 to 10 hours. The resulting support will be free of adsorbed water and should have a surface hydroxyl content from about 0.1 to 5 mmol/g of support, or for example, from 0.5 to 3 mmol/g.

The amount of the hydroxyl groups on silica may be determined according to the method disclosed by J. B. Peri and A. L. Hensley, Jr., in *J. Phys. Chem.*, 72 (8), p. 2926, 1968, the entire contents of which are incorporated herein by reference.

The dried support for a fixed bed catalyst may be compressed into the required shape by compression molding. Depending on the particle size of the support, it may be combined with an inert binder to hold the shape of the compressed part.

Loadings

In some embodiments, the catalyst loading on the support for a fixed bed catalyst provides from 1 to 30 weight % or for example, from 5 to 20 weight %, or for example, from 8 to 15 weight % of said catalyst and from 99 to 70 weight %, or for example, from 80 to 95 weight %, or, for example, from 85 to 92 weight %, respectively, of said support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g., alumina) to form the low surface area supported catalyst.

The catalyst loading for the fluidized bed may be chosen based on a number of factors including the volume of bed, the flow rate of alkane through the bed, energy balance in the bed, binder type, etc. For the fluidized bed catalyst loading may cover a wide range of values ranging from 10 wt. % up to 90 wt. %, or for example, above 20 wt. %, or for example, above 35 wt. %.

The process should be operated to have a conversion of ethane to ethylene of at least 90%, in some instances 95%, or for example, greater than 98% and a selectivity to ethylene of not less than 95%, in some instances greater than 97%.

The Oxidative Dehydrogenation Processes

The catalyst disclosed herein may be used with a fixed bed or a fluidized bed exothermic reaction. The fixed bed reactor is a tubular reactor and in further embodiment the fixed bed reactor comprises multiple tubes inside a shell (e.g., a shell and tube heat exchanger type construction). In a further embodiment, the fixed bed reactor may comprise a number of shells in series and/or parallel. The reactions may involve one or more dehydrogenation steps including oxidative dehydrogenation, and hydrogen transfer steps including oxidative coupling of a hydrocarbon.

In some embodiments, these reactions are conducted at temperatures from about 375° C. up to about 410° C., at pressures from about 100 to 21,000 kPa (15 to 3000 psi), for example, at an outlet pressure from 105 kPa (15 psi) to 172.3 kPa (25 psi), in the presence of an oxidative dehydrogenation catalyst. The hydrocarbon stream may contain a range of compounds including $C_{2-4}$ aliphatic hydrocarbons. The resulting product stream is treated to separate ethylene from the rest of the product stream which may also contain co-products such as acetic acid, and un-reacted feed which is recycled back to the reactor.

Separation

The feed and by products may need to be separated from the product stream. Some processes may use so called dilute ethylene streams. For example, if the product stream does not contain too much ethane, for example, less than about 15 vol. % the stream may be used directly without further purification in a polymerization reactor such as a gas phase, slurry or solution process.

The most common technique would be to use a cryogenic C2 splitter. Other known ethylene/ethane separation techniques could also be used including adsorption (oil, ionic liquids and zeolite).

The present disclosure will now be illustrated by the following non limiting examples.

Figure 1:
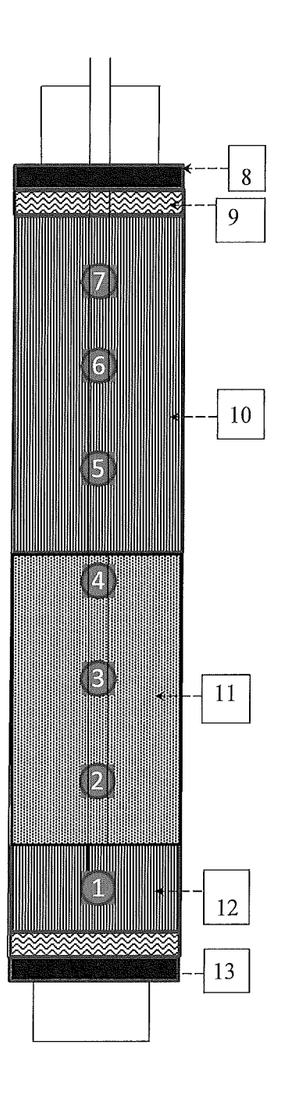
FIG. 1 is a schematic drawing of the reactor used for the testing the ODH catalysts.

In the examples, the fixed bed reactor unit used for the oxidative dehydrogenation reaction is schematically shown in FIG. 1. The reactor was a fixed bed stainless steel tube reactor having a 2 mm (¾") outer diameter and a length of 117 cm (46 inches). The reactor is in an electrical furnace sealed with ceramic insulating material. There are 7 thermocouples in the reactor indicated at numbers 1 through 7. Thermocouples are used to monitor the temperature in that zone of the reactor. Thermocouples 3 and 4 are also used to control the heating of the reactor bed. The feed flows from the top to the bottom of the reactor. At the inlet there is a ceramic cup 8 to prevent air drafts in the reactor. Below the ceramic cup is a layer of quartz wool 9. Below the layer of quartz wool is a layer of catalytically inert quartz powder. Below the quartz powder is the fixed bed 10 comprising catalyst. Below the fixed bed is a layer of quartz powder 11, a layer of quartz wool 12 and a ceramic cup 13. At the exit of the bed was a gas analyzer to determine the composition of the product stream. The GHSV was 2685 hr$^{-1}$ and the pressure was ambient.

For the examples the bed temperature was taken as an average of the temperatures from thermocouples 2, 3 and 4. The feed stream was assumed to have the same temperature as the bed.

EXAMPLES

Comparative Examples

Example 1

Classic Slurry Method
Reaction (Reagents, Mols, Stoichiometry, Solvent, Reaction time, etc.):
$(NH_4)_6Mo_6TeO_{24}.xH_2O$: 6.4 g
$VOSO_4.3.47H_2O$: 3.4 g
$H_3[NbO(C_2O_4)_3]$: 4.56 mmols, 15.82 g of stock solution XG-2365-66 (0.2882 mmol Nb/g solution)

20 ml of distilled water was added to a 100 mL round bottomed flask containing $(NH_4)_6Mo_6TeO_{24}.xH_2O$ (6.4 g) and a stir bar. The slurry dissolved with the aid of a warm water bath (~60° C.).

8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)_6Mo_6TeO_{24}.xH_2O$ solution. The beaker was rinsed with water (2×1 mL) and the rinsed solution was added to the flask. The colorless solution became brown, which was stirred for about 10 minutes under nitrogen.

The $H_3[NbO(C_2O_4)_3]$ solution was added dropwise to above solution with a pipette. A dull-pink slurry formed.

The slurry was evaporated with a slow nitrogen flow while the flask was stirred and placed in a 130° C. silicon oil bath. The color of the slurry turned to grey in about 30 minutes. The bath temperature was raised to 150° C. to drive off the solvent. The flask was then placed in an oven. Temperature was raised from room temperature to 230° C. and kept at 230° C. for 3.3 hours. The flask was cooled to room temperature. The solid was ground, sieved with a 250 µm sieve (9.16 g) and was calcined ($O_2$ level in $N_2$: 0.14 ppm). The black catalyst weighed 6.89 g.

Example 2

Classic Slurry Method as Described in the Literature, Modified by Water Wash Prior to Calcination
Reaction (Reagents, Mols, Stoichiometry, Solvent, Reaction time, etc.):
$(NH_4)_6Mo_6TeO_{24}.xH_2O$: 6.4 g
$VOSO_4.3.47H_2O$: 3.4 g
$H_3[NbO(C_2O_4)_3]$: 4.56 mmols, 15.82 g of stock solution XG-2365-66 (0.2882 mmol Nb/g solution)

20 ml of distilled water was added to a 100 mL round bottomed flask containing $(NH_4)_6Mo_6TeO_{24}.xH_2O$ (6.4 g) and a stir bar. The slurry dissolved with the aid of a warm water bath (~60° C.).

8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)_6Mo_6TeO_{24}.xH_2O$ solution. The beaker was rinsed with water (2×1 mL) and the rinsed solution was added to the flask. The colorless solution became brown, which was stirred for about 10 minutes under nitrogen.

The $H_3[NbO(C_2O_4)_3]$ solution was added dropwise to above solution with a pipette. A dull-pink slurry formed.

The slurry was evaporated with a slow nitrogen flow while the flask was stirred and placed in a 130° C. silicon oil bath. The color of the slurry turned to grey in about 30 minutes. The bath temperature was raised to 150° C. to drive off the solvent. The flask was then placed in an oven. Temperature was raised from room temperature to 230° C. and kept at 230° C. for 3.3 hours. The flask was cooled to room temperature. The solid was ground, sieved with a 250 µm sieve (9.16 g) and was calcined ($O_2$ level in $N_2$: 0.14 ppm). The black powder weighed 6.89 g.

Inventive Examples

Example 3

Reaction
$(NH_4)_6Mo_6TeO_{24}.xH_2O$ (19.2130 g, 15.16 mmol, 1.00 molar equivalents) was dissolved in 60 mL of distilled water in a 250 mL round-bottomed flask with the aid of a warm water bath. The resulting clear and colorless solution was allowed to cool to room temperature.

$VOSO_4.3.47H_2O$ (10.2185 g, 62.69 mmol, 3.08 molar equivalents) was dissolved in 20 mL of distilled water in a 50 mL beaker with the aid of a warm water bath. The resulting clear blue solution formed was cooled to room temperature.

The warm $VOSO_4$ solution was poured into the warm $(NH_4)_6Mo_6TeO_{24}.xH_2O$ solution and a brown solution resulted immediately. The resulting brown solution was stirred under addition of bubbling nitrogen for 20 minutes in a warm water bath.

Aqueous $H_3[NbO(C_2O_4)_3]$ (0.22817 mmols(Nb)/g(solution), 47.4319 g(solution), 13.67 mmols(Nb), 0.903 molar equivalents) was added slowly (dropwise over ten minutes) under $N_2$ bubbling to the brown solution via a pipette over 3 minutes. A dull purple colored slurry formed, which was stirred with bubbling of $N_2$ for 50 minutes.

Hydrothermal Treatment Step
1. The slurry was poured to a 600 mL bare steel high pressure reactor which contained a clean Telfon stir bar. The autoclave was closed and the atmosphere inside of the reactor was evacuated (vacuum) and filled with $N_2$ (20 psi from bulk nitrogen line) 10 times, followed by an additional 10 repeats of purging with $N_2$ (20 psi from bulk nitrogen line) released to a water bubbler. 20 psi nitrogen was left inside reactor and the reactor was sealed.
2. The reactor was attached to condenser and back pressure regulator and the reactor was opened up to this equipment by a needle valve. The regulator was backed all the way out until the 20 psi could be heard to venting from the top of the condenser/back pressure regulator system. The back pressure regulator was then dialed all the way in.

3. The reactor was put into a heating MANTLE setup, where the heat is controlled by heat controller via thermocouples inside and outside the autoclave. The top and bottom of the reactor were wrapped in thermal insulating ceramic fiber tape to ensure proper insulation.

4. The temperature on the heat controller was set to 184° C. The temperature of the reaction was raised to 177° C. over a period of an hour and the back pressure regulator was watched closely. Once the back pressure regulator reached ~170 psi, the regulator knob was backed out until the pressure on the gauge showed 160 psi.

5. The reaction was let to proceed stirring (>500 rpm on the stir plate) at 160 psi and 177° C. for 64 hours. The pressure on the back pressure regulator climbed from 160 psi over the reaction duration.

6. After the completion of the reaction time, the autoclave was cooled to room temperature slowly in the absence of stirring.

7. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

20.3719 g of crude product was obtained for calcination.

Calcination Step

The dried dark purple (almost black) solid was ground a using a mortar/pestle and sieved through a 250 micron porosity sifter. The less than 250 micron particle size dark purple solid was loaded in a quartz boat and the boat was placed into glass furnace tube which is used for calcination. To ensure the exclusion of air during the calcination, the setup was purge under nitrogen for 1 day and then switched to a purified nitrogen flow for 8 hours before beginning the addition of heat. The calcination proceeded under a slow stream (30 ml/min) of purified nitrogen under the following conditions: RT to 600° C. in 4 hours and held at 600° C. for 2 hours. The solid obtained was a black powder, which was ground and sieved through a 250 micron sieve resulting in a powder that was loose and fluffy.

Example 4

Reaction $(NH_4)_6Mo_6TeO_{24} \cdot xH_2O$ (19.2166 g) was dissolved in 60 mL of distilled water in a 250 mL round-bottomed flask with the aid of a warm water bath. The resulting clear and colorless solution was allowed to cool to room temperature.

$VOSO_4 \cdot 3.47H_2O$ (10.2144 g) was dissolved in 20 mL of distilled water in a 50 mL beaker with the aid of a warm water bath. The resulting clear blue solution formed was cooled to room temperature.

The warm $VOSO_4$ solution was poured into the warm $(NH_4)_6Mo_6TeO_{24} \cdot xH_2O$ solution and a brown solution resulted immediately. The resulting brown solution was stirred under addition of bubbling nitrogen for 15 minutes in a warm water bath.

Aqueous $H_3[NbO(C_2O_4)_3]$ (0.35186 mmols(Nb)/g(solution), 38.8874 g(solution)) was added slowly (dropwise over ten minutes) under $N_2$ bubbling to the brown solution via a pipette over 4 minutes. A dull purple colored slurry formed, which was stirred with bubbling of $N_2$ for 120 minutes.

Hydrothermal Treatment Step

1. The slurry was poured to a 600 mL glass lined steel high pressure reactor which contained a clean TEFLON stir bar. The autoclave was closed and the atmosphere inside of the reactor was evacuated (vacuum) and filled with $N_2$ (20 psi from bulk nitrogen line) 10 times, followed by an additional 10 repeats of purging with $N_2$ (20 psi from bulk nitrogen line) released to a water bubbler. 20 psi nitrogen was left inside reactor and the autoclave sealed. The reactor was hooked up to condenser and back pressure regulator setup and the reactor was opened up to this equipment by the needle valve. The regulator was backed all the way out until the 20 psi could be heard to venting from the top of the condenser/back pressure regulator system. The back pressure regulator was then dialed all the way in. The reactor was put into a heating MANTLE setup, where the heat is controlled by heat controller via thermocouples inside and outside the autoclave. The top and bottom of the reactor were wrapped in thermal insulating ceramic fiber tape to ensure proper insulation.

2. The temperature on the heat controller was set to 184° C. The temperature of the reaction was raised to 178° C. over a period of an hour and the back pressure regulator was set to 160 psi.

3. The reaction proceeded with stirring at 160 psi and 178° C. for the 72 hours.

4. After the completion of the reaction time, the autoclave was cooled to room temperature slowly at stand still.

5. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

Calcination Step:

The dried dark purple (almost black) solid was ground a mortar/pestle and sieved through a 250 micron porosity sifter. The less than 250 micron particle size dark purple solid was loaded in a quartz boat and the boat was placed into glass furnace tube which is used for calcination. To ensure the exclusion of air during the calcination, the setup was purge under nitrogen for 1 day and then switched to a purified nitrogen flow for 8 hours before beginning the addition of heat. The calcination proceeded under a slow stream (30 ml/min) of purified nitrogen under the following conditions: RT to 600° C. in 4 hours and held at 600° C. for 2 hours. The solid obtained was a black powder, which was ground and sieved through a 250 micron sieve resulting in a powder that was loose and fluffy.

Example 5

Reaction $(NH_4)_6Mo_6TeO_{24} \cdot xH_2O$ (19.2168 g) was dissolved in 60 mL of distilled water in a 250 mL round-bottomed flask with the aid of a warm water bath. The resulting clear and colorless solution was allowed to cool to room temperature.

$VOSO_4 \cdot 3.47H_2O$ (10.2138 g) was dissolved in 20 mL of distilled water in a 50 mL beaker with the aid of a warm water bath. The resulting clear blue solution formed was cooled to room temperature.

The warm $VOSO_4$ solution was poured into the warm $(NH_4)_6Mo_6TeO_{24}$ solution and a brown solution resulted immediately. The resulting brown solution was stirred under addition of bubbling nitrogen for 30 minutes in a warm water bath. Some precipitation was observed in the solution (solution might have cooled down).

Aqueous $H_3[NbO(C_2O_4)_3]$ (0.35186 mmols(Nb)/g(solution), 38.8930 g(solution)) was added slowly (dropwise over ten minutes) under $N_2$ bubbling to the brown solution via a pipette over 4 minutes. A dull purple colored slurry formed, which was stirred with bubbling of $N_2$ for 10 minutes before being added to the reactor.

Hydrothermal Treatment Step

1. The slurry was poured to a 600 mL bare steel high pressure reactor which contained a clean TEFLON stir bar. The autoclave was closed and the atmosphere inside of the reactor was evacuated (vacuum) and filled with $N_2$ (20 psi from bulk nitrogen line) 10 times, followed by an additional 10 repeats of purging with $N_2$ (20 psi from bulk nitrogen line) released to a water bubbler. 20 psi nitrogen was left inside reactor and the autoclave sealed. The slurry was stirred overnight under 20 psi nitrogen inside the reactor.
2. The reactor was attached to condenser and back pressure regulator and the reactor was opened up to this equipment by a needle valve. The regulator was backed all the way out until the 20 psi could be heard to venting from the top of the condenser/back pressure regulator system. The back pressure regulator was then dialed all the way in. The reactor was put into a heating MANTLE setup, where the heat is controlled by heat controller via thermocouples inside and outside the autoclave. The top and bottom of the reactor were wrapped in thermal insulating ceramic fiber tape to ensure proper insulation.
3. The temperature on the heat controller was set to 184° C. The temperature of the reaction was raised to 170° C. over the period of an hour and the back pressure regulator was set to 160 psi. Over another hour the reaction reached 176° C.
4. The reaction proceeded with stirring at 160 psi and 176° C. for 6 hours.
5. After the completion of the reaction time, the autoclave was cooled to room temperature slowly at stand still.
6. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

Calcination Step

The dried dark purple (almost black) solid was ground a using a mortar/pestle and sieved through a 250 micron porosity sifter. The less than 250 micron particle size dark purple solid was loaded in a quartz boat and the boat was placed into glass furnace tube which is used for calcination. To ensure the exclusion of air during the calcination, the setup was purge under bulk nitrogen for 1 day and then switched to a purified nitrogen flow for 8 hours before beginning the addition of heat. The calcination proceeded under a slow stream (30 ml/min) of purified nitrogen under the following conditions: RT to 600° C. in 4 hours and held at 600° C. for 2 hours. The solid obtained was a black powder, which was ground and sieved through a 250 micron sieve resulting in a powder that was loose and fluffy.

Example 6

Reaction Scheme $(NH_4)_6Mo_6TeO_2 \cdot 7H_2O + 4.13\ VOSO_4 \cdot 3.41H_2O_{(s)} + 0.9\ NbO(C_2O_4H)_{3\ (aq)} \rightarrow ODH\ cat + CO_{2\ (g)} + NH_{3\ (g)}$ Weight of materials used:

| Material Used | Weight (g) | Water (mL) |
|---|---|---|
| $(NH_4)_6Mo_6TeO_2 \cdot 7H_2O_{(s)}$ | 96.00 | 300 |
| $VOSO_4 \cdot 3.41H_2O_{(s)}$ | 70.2197 | 100 |
| $H_3[NbO(C_2O_4)_3]_{(soln.)}$ | 194.35 | |

Reaction Description 96.00 g of $(NH_4)_6Mo_6TeO_2 \cdot 7H_2O_{(s)}$ was dissolved in 300 mL of de-ionized water in a 1 L three neck round bottom flask (RBF), with a stir rate of 750 rpm with a warm water bath.

70.22 g of $VOSO_4 \cdot 3.41H_2O_{(s)}$ was dissolved in 100 mL of de-ionized water, in a warm water bath.

194.35 g of $H_3[NbO(C_2O_4)_3]_{(soln.)}$ was weighed into a 250 mL beaker and held for later use.

$VOSO_4 \cdot 3.41H_2O_{(aq)}$ solution was added to the $(NH_4)_6Mo_6TeO_2 \cdot 7H_2O_{(aq)}$ solution in the 1 L RBF.

Solution turned black.

Solution was left to stir for 30 minutes, after which the solution turned a purple color.

All manipulations were performed in air.

194.35 g of $H_3[NbO(C_2O_4)_3]_{(soln.)}$ was added to a 250 mL addition funnel, affixed to the 3 neck RBF.

Solution was added dropwise to the agitating purple slurry (15 minutes for addition time).

Solution remained as a dark purple slurry.

Solution was transferred to a 2 L glass liner inside a 2 L PARR autoclave and a pill shaped stir bar was added.

Autoclave set up was sealed and purged 10 times with repeating $N_{2\ (g)}$ evacuation sequences.

Autoclave was connected to the condenser set up.

Reaction was left to stir overnight in the autoclave set up at room temperature.

The following day the PARR autoclave was heated to 175° C., the autoclave reached a temperature of 172° C. after 7.5 hours.

Reaction mixture was left in the autoclave set up overnight at 175° C. with the condenser set up.

The following day the temperature was set back to room temperature.

Reaction set up was not cooled by the end of the day and was left to cool over the weekend.

After the reaction was cooled it was depressurized and filtered through 4×Whatmann 4 filter paper media.

The filter cake was rinsed with approximately 0.5 L of deionized water until the filtrate ran clear.

Filtration time was approximately 2 hours.

Filter dried catalyst was dried in the oven at 90° C. overnight.

Dried catalyst was ground and sieved.

Yield: 111 g of pre-catalyst material.

Pre-catalyst material was calcined.

All of the powder was loaded into a quartz tube, which acted as the boat, with some space above to allow gas flow. The quart tube boat was placed inside a larger quartz tube and placed into a unit for calcination. The calcination unit had been thoroughly purged under nitrogen, both bulk and purified to ensure a sufficiently anaerobic environment for calcination. Purified nitrogen flowed over the sample at 150 standard cubic centimeters per minute. The sample was heated from room temperature to 600° C. in 4 hours and held at 600° C. for 4 hours and cooled to room temperature in 4 hours.

Example 7

Reaction Scheme $(NH_4)_6Mo_6TeO_2 \cdot 7H_2O + 4.13\ VOSO_4 \cdot 3.41H_2O_{(s)} + 0.9\ NbO(C_2O_4H)_{3\ (aq)} \rightarrow ODH\ cat + CO_{2\ (g)} + NH_{3\ (g)}$ Reaction Description Identical procedure as for example 6 but used 6 hour hydrothermal reaction time instead of 24 hours.

Example 8

Reaction $(NH_4)_6Mo_6TeO_{24} \cdot xH_2O$ (19.2192 g) was dissolved in 60 mL of distilled water in a 250 mL round-bottomed flask with the aid of a warm water bath. The resulting clear and colorless solution was allowed to cool to room temperature.

VOSO$_4$.3.47H$_2$O (10.1680 g) was dissolved in 20 mL of distilled water in a 50 mL beaker with the aid of a warm water bath. The resulting clear blue solution formed was cooled to room temperature.

The warm VOSO$_4$ solution was poured into the warm (NH$_4$)$_6$Mo$_6$TeO$_{24}$.xH$_2$O solution and a brown solution resulted immediately. The resulting brown solution was stirred under addition of bubbling nitrogen for 15 minutes in a warm water bath.

Aqueous H$_3$[NbO(C$_2$O$_4$)$_3$] (0.35186 mmols(Nb)/g(solution), 38.8700 g(solution)) was added slowly (dropwise over ten minutes) under N$_2$ bubbling to the brown solution via a pipette over 3 minutes. A dull purple colored slurry formed, which was stirred with bubbling of N$_2$ for 90 minutes.

Hydrothermal Treatment Step

1. The slurry was poured to a 600 mL bare steel high pressure reactor without a stir bar. The autoclave was closed and the atmosphere inside of the reactor was evacuated (vacuum) and filled with N$_2$ (20 psi from bulk nitrogen line) 10 times, followed by an additional 10 repeats of purging with N$_2$ (20 psi from bulk nitrogen line) released to a water bubbler. 20 psi nitrogen was left inside reactor and the autoclave sealed. The reactor was attached to a condenser and back pressure regulator setup and the reactor was opened up to this equipment by the needle valve. The regulator was backed all the way out until the 20 psi could be heard to venting from the top of the condenser/back pressure regulator system. The back pressure regulator was then dialed all the way in. The reactor was put into a heating MANTLE setup, where the heat is controlled by heat controller via thermocouples inside and outside the autoclave. The top and bottom of the reactor were wrapped in thermal insulating ceramic fiber tape to ensure proper insulation.
2. The temperature on the heat controller was set to 184° C. The temperature of the reaction was raised to 178° C. over the period of an hour and the back pressure regulator was set to 160 psi.
3. The reaction proceeded with no stirring at 160 psi and 178° C. for the 72 hours.
4. After the completion of the reaction time, the autoclave was cooled to room temperature slowly.
5. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

Calcination Step

The dried dark purple (almost black) solid was ground using a mortar/pestle and sieved through a 250 micron porosity sifter. The less than 0.25 micron particle size dark purple solid was loaded in a quartz boat and the boat was placed into glass furnace tube which is used for calcination. To ensure the exclusion of air during the calcination, the setup was purge under nitrogen for 1 day and then switched to a purified nitrogen flow for 8 hours before beginning the addition of heat. The calcination proceeded under a slow stream (30 ml/min) of purified nitrogen under the following conditions: RT to 600° C. in 4 hours and held at 600° C. for 2 hours. The solid obtained was a black powder, which was ground and sieved through a 250 micron sieve resulting in a powder that was loose and fluffy.

Example 9

Reaction (NH$_4$)$_6$Mo$_6$TeO$_{24}$.xH$_2$O (19.2103 g, 15.16 mmol, 1.00 molar equivalents) was dissolved in 60 mL of distilled water in a 250 mL round-bottomed flask with the aid of a warm water bath. The resulting clear and colorless solution was allowed to cool to room temperature.

VOSO$_4$.3.47H$_2$O (10.2128 g, 46.70 mmol, 3.08 molar equivalents) was dissolved in 25 mL of distilled water in a 50 mL beaker with the aid of a warm water bath. The resulting clear blue solution formed was cooled to room temperature.

The VOSO$_4$ solution was poured into the (NH$_4$)$_6$Mo$_6$TeO$_{24}$.xH$_2$O solution and a brown solution resulted immediately. The beaker which contained the VOSO$_4$ solution was rinsed with two 1 mL aliquots of water and these rinsings were added to the flask. The resulting brown solution was stirred under addition of bubbling nitrogen for 25 minutes.

Aqueous H$_3$[NbO(C$_2$O$_4$)$_3$] (0.2882 mmols(Nb)/g(solution), 47.4365 g(solution), 13.67 mmols(Nb), 0.903 molar equivalents) was added slowly (dropwise over ten minutes) under N$_2$ bubbling to the brown solution via a pipette over 3 min. A dull purple colored slurry formed, which was stirred with bubbling of N$_2$ for 35 minutes.

Hydrothermal Treatment Step

The slurry was poured to a 600 mL bare steel high pressure reactor which contained a clean TEFLON stir bar. The autoclave was closed and the atmosphere inside of the reactor was evacuated (vacuum) and filled with N$_2$ (20 psi from bulk nitrogen line) 10 times, followed by an additional 10 repeats of purging with N$_2$ (20 psi from bulk nitrogen line) and releasing of N$_2$ pressure (positive pressure relief) to a water bubbler. The autoclave was left under ambient pressure of N$_2$ atmosphere and the vessel was sealed.

The reactor was put into a heating MANTLE setup, where the heat is controlled by heat controller via thermocouples inside and outside the autoclave. The top and bottom of the reactor were wrapped in thermal insulating ceramic fiber tape to ensure proper insulation. The temperature was raised to 175° C. over a period of an hour and the reaction was proceeded with stirring (>500 on the stir plate), at this temperature for 48 hours.

After the completion of the reaction time, the autoclave was cooled to room temperature slowly while still stirring the reaction contents. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

Calcination Step

The dried dark purple (almost black) solid was ground using a mortar/pestle and sieved through a 250 micron porosity sifter. The less than 0.25 micron particle size dark purple solid was loaded in a quartz boat and the boat was placed into glass furnace tube which is used for calcination. To ensure the exclusion of air during the calcination, the setup was purge under nitrogen for 1 day and then switched to a purified nitrogen flow for 8 hours before beginning the addition of heat. The calcination proceeded under a slow stream (30 ml/min) of purified nitrogen under the following conditions: RT to 600° C. in 4 hours and held at 600° C. for 2 hours. The solid obtained was a black powder, which was ground and sieved through a 250 micron sieve resulting in a powder that was loose and fluffy.

The catalysts were then used as a fixed bed in an ODH reactor, as described above, in which the same feed was feed to each experiment. The results of the ODH reactor are set forth in Table 1

TABLE 1

Catalyst Performance Results Comparing Examples

| | Example 1<br>Classic Slurry Method as<br>described in literature | | Example 2<br>Classic Slurry Method<br>with a water wash | | Example 3<br>(High Pressure Gas<br>Release Method on 20 g<br>Scale in bare SS Reactor-<br>72 hours rxn time) | | Example 4<br>(High Pressure Gas<br>Release Method on 20 g<br>Scale in Glass Lined Reactor-<br>72 hours rxn time) | | Example 5<br>(High Pressure Gas<br>Release Method on 20 g<br>Scale in Glass Lined Reactor-<br>6 hours rxn time) | |
|---|---|---|---|---|---|---|---|---|---|---|
| | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion |
| | 444.0 | 95.0 | 465.0 | 94.0 | 376.3<br>385.3<br>AVG 380.8<br>MIN 376.3<br>MAX 385.3<br>Diff: 9 | 96.3<br>96.0<br>96.15<br>96.00<br>96.3<br>0.3 | 384.3 | 96.5 | 371.2 | 97.0 |

| | Example 6<br>High Pressure Gas<br>Release Method on 100 g<br>Scale in Glass Lined<br>Reactor using stir bar-<br>24 hours rxn time) | | Example 7<br>High Pressure Gas<br>Release Method in<br>Glass Lined Reactor<br>using stir bar-<br>6 hours rxn time) | | Example 8<br>High Pressure<br>Reflux Method<br>(same method<br>as Example 3)<br>BUT no stirring | | Example 9<br>Sealed Reactor<br>System, i.e. no<br>refluxing but stirred | | Example 10<br>Classic Slurry Method as<br>described in literature | | Example 11<br>Classic Slurry Method<br>with a water wash | |
|---|---|---|---|---|---|---|---|---|---|---|---|---|
| | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion | Temperature at which 25% Conversion is obtained | Selectivity at 25% Conversion |
| | 368.5<br>358.2<br>365.9 | 97.7<br>97.1<br>97.1 | 358.3<br>372.4<br>365.6 | 98.0<br>97.0<br>97.0 | 435.4 | 86.7 | 432.1 | 92.5 | 444.0 | 95.0 | 465.0 | 94.0 |
| AVG | 364.20 | 97.28 | 365.43 | 97.33 | | | | | | | | |
| MIN | 358.21 | 97.05 | 358.30 | 97.00 | | | | | | | | |
| MAX | 368.50 | 97.70 | 372.40 | 98.00 | | | | | | | | |
| RANGE | 10.29 | 0.65 | 14.1 | 1 | | | | | | | | |

What is claimed is:

1. A process for synthesis of a catalyst for oxidative dehydrogenation of paraffins via a hydrothermal treatment comprising:
   i) preparing an aqueous slurry comprising Mo, V, Nb and Te salts in a molar ratio of metal elements 1:0.3 to 3; 0.05 to 0.25; and 0.08 to 0.2 at a temperature from 25° C. to 80° C.;
   ii) heating the slurry in a reactor to a temperature from 80° to 220° C. at a pressure equal or above the saturated water vapor pressure at the corresponding reaction temperature, for a period of time not less than 1 hour with agitation and simultaneous removal of gaseous byproduct species produced during the reaction;
   iii) letting the reactor cool and depressurizing the reactor and recovering the catalyst as a solid.

2. The process according to claim 1, wherein the temperature of the reactor is from 150° C.-185° C.

3. The process according to claim 2, wherein the pressure in the reactor is from 10 psi to 190 psi (960 kPa to 1300 kPa).

4. The process according to claim 1, wherein there is a condenser upstream of a pressure control device.

5. The process according to 4, wherein the condenser is operated at a temperature above 0° C. and below reaction temperature.

6. The process according to claim 1, wherein the gaseous byproduct species are removed by being vented from the reactor through a pressure control device.

7. The process according to claim 1, wherein the gaseous byproduct species are removed from the reactor using one or more methods selected from gas absorption, gas adsorption, membrane separation, and chemicals transformation.

8. The process according to claim 1 wherein the time of hydrothermal treatment is from 1 to 72 hours.

9. The process according to claim 8, wherein the reactor is metal.

10. The process according to claim 9, wherein the reactor can be lined or the reactor contains glass fibers, beads, or other nucleating agents.

11. The process according to claim 10, wherein the reactor is lined and the lining comprises one or more of ceramic based material, a different metal, fluorocarbon polymers and combinations thereof.

12. The process according to claim 11, wherein the aqueous slurry comprises a molar ratio Mo, V, Nb and Te salts 1: 0.5 to 1.0: 0.08 to 0.20: 0.10 to 0.20.

13. The process according to claim 12, wherein step iii) further includes separating a resulting precatalyst from the aqueous phase and washing it with distilled water or an aqueous oxalate solution and drying the precatalyst to form the catalyst.

14. The process according to claim 13, further comprising grinding the catalyst.

15. The process according to claim 14, further including step iv) calcining the catalyst in an inert atmosphere at a temperature from 200° C. to 650° C. for a time from 1 to 20 hours.

16. The process according to claim 15 wherein the calcined catalyst comprises the following molar ratios: Mo1:V 0.32-0.49:Te 0.10-0.17:Nb 0.14-0.17 as determine by PIXE.

* * * * *